US006500434B1

(12) United States Patent
Langermann et al.

(10) Patent No.: US 6,500,434 B1
(45) Date of Patent: Dec. 31, 2002

(54) CHAPERONE AND ADHESIN PROTEINS; VACCINES, DIAGNOSTICS AND METHOD FOR TREATING INFECTIONS

(75) Inventors: Solomon Langermann, Baltimore, MD (US); Scott J. Hultgren, Ballwin, MO (US); Jerome S. Pinkner, St. Louis, MO (US); Christine Gale Auguste, Germantown, MD (US)

(73) Assignee: MedImmune, Inc., Gaithersburg, MD (US)

( * ) Notice: Subject to any disclaimer, the term of this patent is extended or adjusted under 35 U.S.C. 154(b) by 0 days.

(21) Appl. No.: 09/298,494

(22) Filed: Apr. 23, 1999

Related U.S. Application Data
(60) Provisional application No. 60/082,824, filed on Apr. 23, 1998.

(51) Int. Cl.[7] ...................... A61K 39/385; A61K 39/38; A61K 39/02
(52) U.S. Cl. ................. 424/197.11; 424/184.1; 424/192.1; 424/193.1; 424/234.1; 424/242.1; 424/257.1; 424/200.1; 424/203.1; 424/241.1; 530/402
(58) Field of Search ........................... 424/184.1, 234.1, 424/192.1, 193.1, 197.11, 242.1, 257.1, 200.1, 203.1, 241.1; 530/402

(56) References Cited

PUBLICATIONS

Hung Et Al. EMBO Journal 15(15): 3792–3805, 1996.*
Hultgren Et Al. Proc. Natl. Acad. Sci 86: 4357–4361, 1988.*
Jones Et Al. Proc. Natl. Acad. Sci 90: 8397–8401, 1993.*
Langermann Et Al. Science 276(5312): 607–611, (Apr. 25, 1997).*
Knight Et Al. Acta Crystallographica Section D Biological Crystallography 53(2):207–210, 1997.
Saulino Et Al. EMBO Journal 17(8): 2177–2185, Apr. 15, 1998.
Madison. Dissertation 1990 (Abstract).
Madison Et Al, Abstract of the Annual Meeting of the American Society for Microbiology 1989.
Tweari Et Al. Journal of Biological Chemistry 268(4): 3009–3015, 1993.*
Palaszynski Et Al. Dev. Biol. Stand 92:117–122, 1998.*
Thankarel Et Al. Journal of Clinical Investigations 100(5): 1123–1136, 1997.*

Abraham Et Al. Nature 336(6200):682–684,1988.*
Hung, D.L., "Molecular Basis of Two Subfamilies of Immunoglobulin–like Chaperones," *The EMBO Journal*, vol. 15, No. 15, p. 3792–3805 (1996).
Hultgren Scott J., "The PapG adhesin of Uropathogenic *Escherichia coli* Contains Separate Regions for Receptor Binding and for the Incorporation into the Pilus", *Proc. Natl. Acad. Sci, USA*, vol. 86, pp. 4357–4361 (Jun. 1989).
O'Hanley, Peter., "Molecular Basis of *Escherichia coli* Colonization of the Upper Urinary Tract in BALB/c Mice", vol. 75, p. 347–360 (Feb. 1985).
Roberts, James A., "The Gal($\alpha$1–4) Gal–specific Tip Adhesin of *Escherichia coli* P–fimbriae is Needed for Pyelonephritis to Occur in the Normal Urinary Tract", vol. 91, p. 11889–11893 (Dec. 1994).
Jones, C. Hal., "FimC is a Periplasmic PapD–like Chaperone that Directs Assembly of Type 1 Pili in Bacteria", *Proc. Natl. Acad. Sci. USA*, vol. 90, p. 8397–8401 (Sep. 1993).
Abraham, Soman N., "Protection Against *Escherichia coli*–Induced Urinary Tract Infections with Hybridoma Antibodies Directed Against Type 1 Fimbriae or Complementary D–Mannose Receptors", *Infection and Immunity*, pp. 625–628 (Jun. 1985).
Langermann, S. et al., "Prevention of Mucosal *Escherichia coli* Infection by FimH–Adhesin–Based Systemic Vaccination," *Science*, pp. 607–611, vol. 276, 25 (Apr. 1997).
Jones, C. Hal., et al., "FimC is a periplasmic PapD–like chaperone that directs assembly of type 1 pili in bacteria," *Proc. National Acad. Sci. USA*, pp. 8397–8401, vol. 90 (Sep. 1993).

* cited by examiner

*Primary Examiner*—Anthony C. Caputa
*Assistant Examiner*—Anne L. Holleran
(74) *Attorney, Agent, or Firm*—Elliot M. Olstein; Alan J. Grant

(57) ABSTRACT

The present invention provides bacterial immunogenic agents for administration to humans and non-human animals to stimulate an immune response. It particularly relates to the vaccination of mammalian species with heteropolymeric protein complexes as a mechanism for stimulating production of antibodies that protect the vaccine recipient against infection by pathogenic bacterial species. In another aspect the invention provides antibodies against such proteins and protein complexes that may be used as diagnostics and/or as protective/treatment agents for pathogenic bacterial species. A novel vector for expressing the FimC-H complex at optimal levels is also disclosed.

37 Claims, 4 Drawing Sheets

Groups of challenged mice

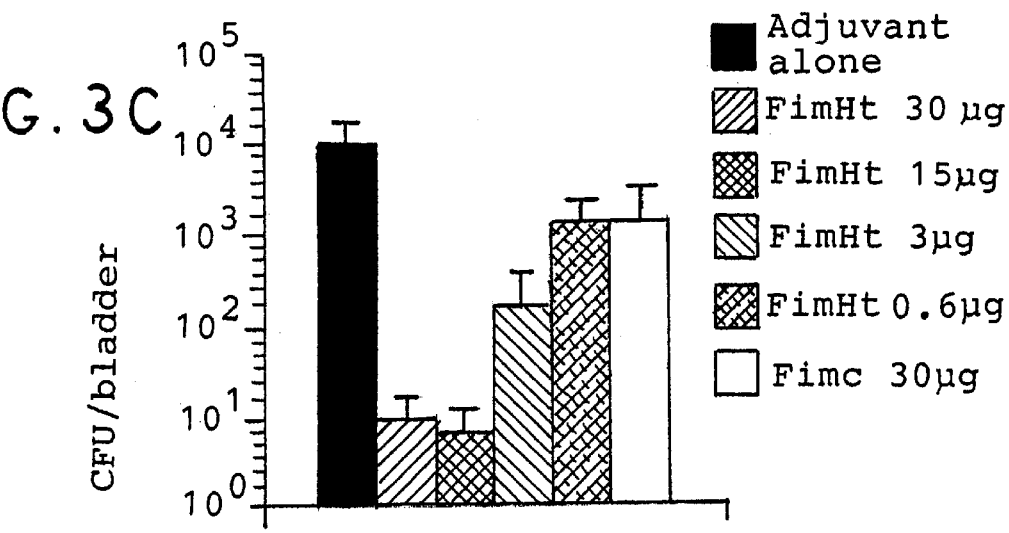
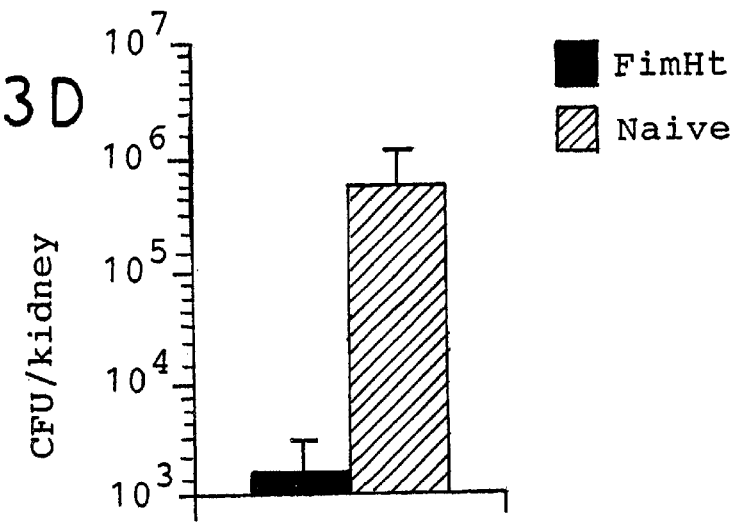
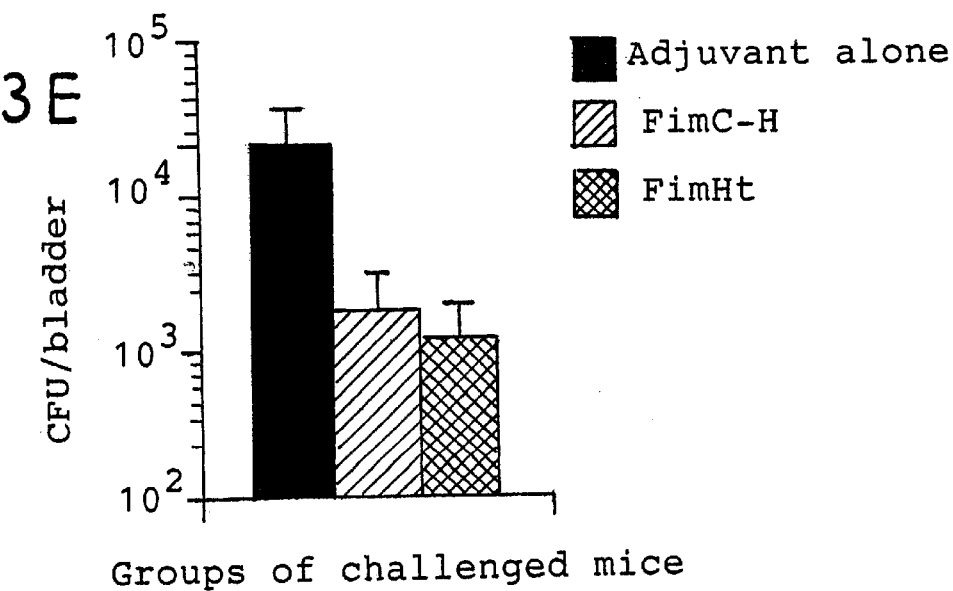
Groups of challenged mice

SEQUENCE LISTING

<160> NUMBER OF SEQ ID NOS: 2

<210> SEQ ID NO 1
<211> LENGTH: 957
<212> TYPE: DNA
<213> ORGANISM: Escherichia coli

<400> SEQUENCE: 1

```
atgaaacgag ttattaccct gtttgctgta ctgctgatgg gctggtgcgt aaatgcctgg      60
tcattcgcct gtaaaaccgc caatggtacc gctatcccta ttggcggtgg cagcgccaat     120
gtttatgtaa accttgcgcc cgtcgtgaat gtggggcaaa acctggtcgt ggatctttcg     180
acgcaaatct tttgccataa cgattatccg gaaaccatta cagactatgt cacactgcaa     240
cgaggctcgg cttatggcgg cgtgttatct aatttttccg ggaccgtaaa atatagtggc     300
```

-continued

```
agtagctatc catttcctac caccagcgaa acgccgcgcg ttgtttataa ttcgagaacg    360
gataagccgt ggccggtggc gctttatttg acgcctgtga gcagtgcggg cggggtggcg    420
attaaagctg gctcattaat tgccgtgctt aggttgcgac agaccaacaa ctataacagc    480
gatgatttcc agtttgtgtg aatatttac gccaataatg atgtggtggt gcctactggc     540
ggctgcgatg tttctgctcg tgatgtcacc gttactctgc cggactaccg tggttcagtg    600
ccaattcctc ttaccgttta tcgtgcgaaa agccaaaacc tggggtatta cctctccggc    660
acacacgcag atgcgggcaa ctcgattttc accaataccg cgtcgttttc acctgcacag    720
ggcgtcggcg tacagttgac gcgcaacggt acgattattc cagcgaataa cacggtatcg    780
ttaggagcag tagggacttc ggcggtgagt ctgggattaa cggcaaatta tgcacgtacc    840
ggagggcagg tgactgcagg gaatgtgcaa tcgattattg gcgtgacttt tgtttatcaa    900
taaagaaatc acaggacatt gctaatgctg gtacgcaata ttacctgaag ctaaaaa      957
```

<210> SEQ ID NO 2
<211> LENGTH: 300
<212> TYPE: PRT
<213> ORGANISM: Escherichia coli

<400> SEQUENCE: 2

```
Met Lys Arg Val Ile Thr Leu Phe Ala Val Leu Leu Met Gly Trp Ser
  1               5                  10                  15

Val Asn Ala Trp Ser Phe Ala Cys Lys Thr Ala Asn Gly Thr Ala Ile
                 20                  25                  30

Pro Ile Gly Gly Gly Ser Ala Asn Val Tyr Val Asn Leu Ala Pro Val
             35                  40                  45

Val Asn Val Gly Gln Asn Leu Val Val Asp Leu Ser Thr Gln Ile Phe
         50                  55                  60

Cys His Asn Asp Tyr Pro Glu Thr Ile Thr Asp Tyr Val Thr Leu Gln
 65                  70                  75                  80

Arg Gly Ser Ala Tyr Gly Gly Val Leu Ser Asn Phe Ser Gly Thr Val
                 85                  90                  95

Lys Tyr Ser Gly Ser Ser Tyr Pro Phe Pro Thr Thr Ser Glu Thr Pro
            100                 105                 110

Arg Val Val Tyr Asn Ser Arg Thr Asp Lys Pro Trp Pro Val Ala Leu
        115                 120                 125

Tyr Leu Thr Pro Val Ser Ser Ala Gly Gly Val Ala Ile Lys Ala Gly
    130                 135                 140

Ser Leu Ile Ala Val Leu Ile Leu Arg Gln Thr Asn Asn Tyr Asn Ser
145                 150                 155                 160

Asp Asp Phe Gln Phe Val Trp Asn Ile Tyr Ala Asn Asn Asp Val Val
                165                 170                 175

Val Pro Thr Gly Gly Cys Asp Val Ser Ala Arg Asp Val Thr Val Thr
            180                 185                 190

Leu Pro Asp Tyr Arg Gly Ser Val Pro Ile Pro Leu Thr Val Tyr Cys
        195                 200                 205

Ala Lys Ser Gln Asn Leu Gly Tyr Tyr Leu Ser Gly Thr His Ala Asp
    210                 215                 220

Ala Gly Asn Ser Ile Phe Thr Asn Thr Ala Ser Phe Ser Pro Ala Gln
225                 230                 235                 240

Gly Val Gly Val Gln Leu Thr Arg Asn Gly Thr Ile Ile Pro Ala Asn
                245                 250                 255
```

-continued

```
Asn Thr Val Ser Leu Gly Ala Val Gly Thr Ser Ala Val Ser Leu Gly
            260                 265                 270

Leu Thr Ala Asn Tyr Ala Arg Thr Gly Gly Gln Val Thr Ala Gly Asn
        275                 280                 285

Val Gln Ser Ile Ile Gly Val Thr Phe Val Thr Gln
    290                 295                 300
```

CHAPERONE AND ADHESIN PROTEINS; VACCINES, DIAGNOSTICS AND METHOD FOR TREATING INFECTIONS

This Application claims the priority of Provisional Application Ser. No. 60/082,824, filed Apr. 23, 1998.

BACKGROUND OF THE INVENTION

This invention relates generally to the field of bacterial antigens and their use, for example, as immunogenic agents in humans and animals to stimulate an immune response. More specifically, it relates to the vaccination of mammalian species with heteropolymeric protein complexes as a mechanism for stimulating production of antibodies that protect the vaccine recipient against infection by pathogenic bacterial species, including all types of enterobacteriacea.

In a particular aspect, the present invention relates to the prevention and treatment of urinary tract infections such as cystitis and/or pyelonephritis that are caused by pilus-carrying bacteria (uropathogenic bacteria). In this regard, certain types of *Escherichia coli* are of particular interest since they are the predominant etiologic agent of urinary tract infections (UTIs).

UTIs provide one example of a disease process that is mediated (or assisted) by the attachment to bacteria to cells. *E. coli* is the most common pathogen of the urinary tract, accounting for greater than 85% of cases of asymptomatic bacteriuria, acute cystitis and acute pyelonephritis, as well as greater than 60% of recurrent cystitis, and at least 35% of recurrent pyelonephritis infections. Furthermore, approximately 25%–30% of women experience a recurrent *E. coli* urinary tract infection within the first 12 months following an initial infection: after a second or third infection the rate of recurrence increases to 60%–75%. Given the high incidence, continued persistence, and significant expense associated with *E. coli* urinary tract infections, there is a need for a prophylactic vaccine to reduce susceptibility to this disease.

While many factors contribute to the acquisition and progression of *E. coli* urinary tract infections, it is widely accepted that colonization of the urinary epithelium is a prerequisite to infection. In a typical course of *E. coli* urinary tract infection, bacteria originate from the bowel, ascend into the bladder, and adhere to the bladder mucosa where they multiply and establish an infection (cystitis) before ascending into the ureters and kidneys. Disruption or prevention of pilus-mediated attachment of *E. coli* to urinary epithelia may prevent or retard the development of urinary tract infections. In this regard, a number of studies have pointed to a role for pili in mediating attachment to host uroepithelial cells.

To initiate infection bacterial pathogens must first be able to colonize an appropriate target tissue of the host. For many pathogens this tissue is located at a mucosal surface. Colonization begins with the attachment of the bacterium to receptors expressed by cells forming the lining of the mucosa. Attachment is mediated via proteins on the bacterium that bind specifically to cellular receptors. These proteins, or adhesins, are expressed either directly on the surface of the bacterium, or more typically, as components of elongated rod-like protein structures called pili, fimbriae or fibrillae.

Type 1 pili are thought to be important in initiating colonization of the bladder and inducing cystitis, whereas P pili are thought to play a role in ascending infections and the ensuing pyelonephritis.

Such pili are heteropolymeric structures that are composed of several different structural proteins required for pilus assembly. Two types of pili are of particular interest: P pili and type 1 pili. P pili-carrying bacteria recognize and bind to the gal$\alpha$(1–4)gal moiety present in the globoseries of glycolipids on kidney cells in mammals. Type 1 pili-carrying bacteria recognize and bind to D-mannose in glycolipids and glycoproteins of bladder epithelial cells.

PapG, the adhesin protein in P pili bacteria that mediates the specific interaction of the pilus with receptors on the surface of host cells, is found at the distal end of the tip fibrillum. Its periplasmic chaperone protein is PapD which is highly conserved across strains of *E. coli*. (Hultgren et al., Proc. Natl. Acad. Sci. USA 86:4357 (1989); EMBO Journal 15:3792–3805 (1996).

With regard to type 1 pili, tip adhesins and other ancillary subunits also have been identified. FimH is the D-mannose-binding adhesin that promotes attachment of type 1-piliated bacteria to host cells via mannose-containing glycoproteins on eukaryotic cell surfaces. FimC is its periplasmic chaperone protein. FimH is also highly conserved not only among uropathogenic strains of *E. coli*, but also among a wide range of gram-negative bacteria. For example, all Enterobacteriacea produce FimH. Thus, vaccines incorporating the FimH antigen should exhibit a broad spectrum of protection.

Chaperone proteins are a class of proteins in gram-negative bacteria that are involved in the assembly of pili by mediating such assembly, but are not incorporated into the structure. PapD is the periplasmic chaperone protein mediating the assembly of pili for P piliated bacteria and FimC is the periplasmic chaperone protein that mediates assembly of type 1 pili in bacteria.

Antibodies directed against purified whole type 1 or P pili protect against cystitis and pyelonephritis, respectively, in both murine and primate models for these diseases. Abraham et al., Infect Immun. 48:625 (1985), Roberts et al., Proc. Natl. Acad. Sci. (USA) 91:11889 (1994), O'Hantey et al., J. Clin. Invest. 75: 347 (1985). However, such protection is limited to either homologous *E. coli* strains from which the pili used as immunogens were derived, or to a small subset of serologically cross-reactive heterologous strains. Therefore, vaccines composed predominantly of the major structural proteins of pili (i.e., PapA or FimA) appear to be of limited value because antibodies developed against these highly variable proteins are specific for the strains used for immunization.

BRIEF SUMMARY OF THE INVENTION

In one aspect the present invention relates to a vaccine for treating or preventing bacterial infections which utilizes as an immunogen a complex of a bacterial periplasmic chaperone protein with a bacterial adhesin protein. Preferably, the adhesin protein is a pilus adhesin protein. In one embodiment, the periplasmic chaperone protein and pilus adhesin protein are from *E. coli*; for example, a member selected from the complexes PapD/PapG and FimC/FimH.

In a particular aspect, the invention relates to vaccines formulated from type 1 pilus-associated adhesins (or from mannose-binding fragments thereof) or from complexes of chaperone proteins (including PapD-like chaperones) and pilus-associated adhesins for the treatment and/or prophylaxis of diseases caused by pathogenic species of gram-negative bacteria, such as *Escherichia coli* (*E. coli*). For example, it relates to treatment and/or prophylaxis of urinary tract infections caused by *E. coli* with vaccines formulated from at least one of (1) a fragment of the pilus-associated adhesin FimH that retains mannose binding capability (alone or complexed with its chaperone FimC), (2) the pilus-associated adhesin PapG protein complexed with its periplasmic chaperone protein PapD or (3) the full-length pilus-associated adhesin FimH (alone or in a complex with its chaperone protein FimC). This invention also relates generally to the use of heteropolymeric protein complexes to raise antibodies in non-human mammalian species useful, for example, as diagnostic reagents and vaccines.

In yet another aspect, the present invention relates to the production of essentially full-length bacterial adhesin proteins in a recombinant host (in *E. coli*, another bacterial species, a bacterial species with one or more disabled proteases, or a non-bacterial production vector or host cell) or by synthesis. Such recombinant or synthetic methods permit the production of the full-length adhesin protein in the presence or absence of its chaperone protein and when chaperones are absent preferably in the absence of proteases that will shorten its length or start to break it down. Even more preferable is the production of essentially full-length FimH or a mannose binding analog or variant for use as a vaccine. If such recombinant production is performed in a host which is capable of producing an usher protein, the recombinant production is under conditions which eliminate usher production.

Using novel methods disclosed herein, it is possible to recombinantly introduce into a bacterial cell the Fimh and FimC genes using a single vector, commonly a plasmid but in no way limited thereto.

In a yet further aspect, the present invention relates to the production of mannose-binding fragments of bacterial adhesin proteins in a recombinant host (in *E. coli*, another bacterial species, or a non-bacterial production vector or host cell) or by synthesis. Preferably, when such protein fragments are expressed in a bacterial host that produces an usher protein they are expressed under such conditions that their usher protein is not expressed. Such recombinant or synthetic methods permit the production of mannose-binding adhesin protein fragments in the absence of the their chaperone protein or as a complex with their chaperone protein that can later be separated from the chaperone protein. Preferably, such fragments are produced under conditions that avoid shortening of their length by cleavage or break down by proteases.

In another aspect, the proteins are produced with a histidine label (or other suitable label) such that the full-length proteins or fragments can be isolated due to their label.

In a further aspect, the present invention relates to the production of a periplasmic chaperone protein in a complex with an essentially full-length bacterial adhesin protein or appropriate fragment thereof in a recombinant host (in *E. coli*, another bacterial species, a bacterial species with one or more disabled proteases, or a non-bacterial production vector or host cell) or by synthesis or by recovering from a natural source. Even more preferable is the production of the periplasmic chaperone protein FimC complexed with essentially full-length FimH or a mannose binding analog or variant for use as a vaccine.

In another aspect the present invention relates to a method of prophylaxis and/or treatment of diseases that are mediated by pili-bearing bacteria that have adhesin proteins. In particular, the invention relates to a method for the prophylaxis and/or treatment of infectious diseases that are mediated by type 1 pili adhesin proteins. In a still further preferred aspect, the invention relates to a method for the prophylaxis and/or treatment of UTIs in humans, particularly in women or children.

In still another aspect the present invention relates to a method of using one or more antibodies (monoclonal, polyclonal or sera) to either a periplasmic chaperone protein or fragment thereof complexed with an adhesin protein or an adhesin protein (alone) for the prophylaxis and/or treatment of diseases that are mediated by pili-bearing bacteria that have adhesin proteins. In particular, the invention relates to a method for the prophylaxis and/or treatment of infectious diseases that are mediated by type 1 pili adhesin proteins. In a still further preferred aspect, the invention relates to a method for the prophylaxis and/or treatment of UTIs in humans, particularly in women or children, by utilizing antibodies to either the periplasmic chaperone protein FimC complexed with the adhesin protein FimH (anti-FimC-H) or the adhesin protein FimH alone (anti-FimH).

BRIEF DESCRIPTION OF THE DRAWINGS

FIG. 2 shows Type 1-piliated [HB1 O1/pSH2 (black bars) and non-piliated (cross-hatched)] bacteria which were directly labeled with FITC and tested for their ability to bind to bladder cells at various dilutions. FIGS. 2B and 2C, respectively, illustrate the ability of anti-FimH and anti-FimC-H antibodies to inhibit the binding of such type 1-piliated *E. coli* to human bladder epithelial cells.

FIGS. 3–3E report the data in the C3 H/HaJ murine cystitis model for protection of anti-FimH or anti-FimC-H antibodies in vivo against bladder and kidney infections. FIGS. 3 and 3B show the results of in vivo CFU/bladder counts of type 1-pilated FimH+*E. coli* (NU14) type 1-pilated FimH- *E. coli* (NU14–1) at various dilutions in unprotected mice. FIG. 3C shows the CFU/bladder in vivo results for mice challenged with NU14 *E. coli* after having been injected with (histograms from left to right, respectively) adjuvant alone, FimHt 30 µg, FimHt 15 µg, FimHt 3 µg, FimHt 0.05 µg and FimC 30 µg. FIG. 3D shows the protective ability of anti-FimHt in mice injected with FimHt against the progression of infection from the bladder to the kidney as contrasted with naive mice who do not produce anti-FimHt. FIG. 3E shows the protective effects of anti-FimHt antisera in mice challenged with NU14 bacteria. The anti-FimC-H appeared to give slightly better protection than FimHt.

DETAILED DESCRIPTION OF THE INVENTION

Figure 1A:
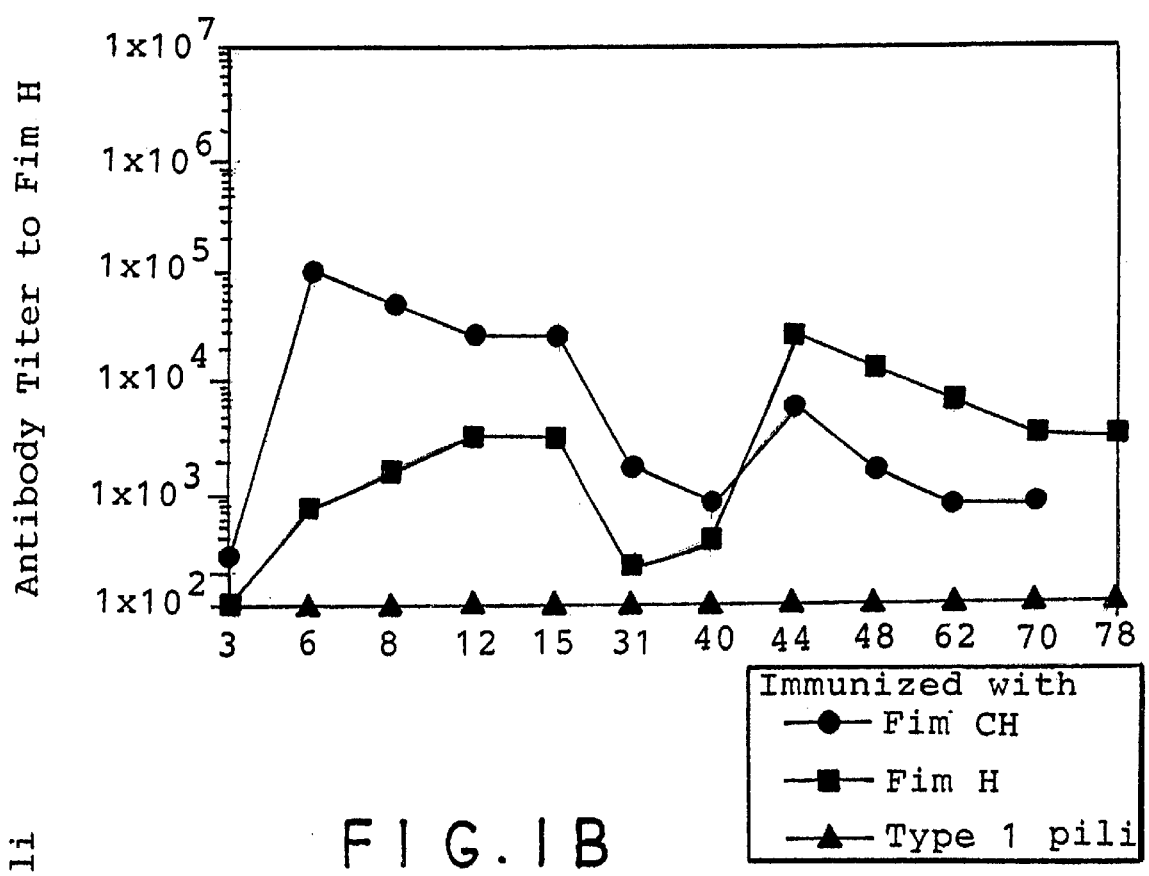
FIGS. 1A and 1B show data results of immunoglobulin G (IgG) titer to FimHt adhesin and whole type 1 pili, respectively, up to 78 weeks post immunization with purified adhesin, adhesin-chaperone complex or whole type 1 pili, further described in Example 1.

It is an object of the present invention to utilize as immunogenic composition for a vaccine (or to produce antibodies for use as a diagnostic or as a passive vaccine) comprising a bacterial adhesin protein or a complex of a bacterial periplasmic chaperone protein and such a bacterial adhesin protein. In one embodiment, proteins (naturally or recombinantly produced, as well as functional analogs) from bacteria that produce type 1 pili are contemplated. Even more particularly, *E. coli* proteins are contemplated.

A particularly preferred embodiment of such an immunogenic composition is for use as a vaccine (or as an immunogen for producing antibodies useful for diagnostics or vaccines) wherein the active component of the immunogenic composition is a member selected from mannose-binding fragments of FimH adhesin protein (alone or complexed with a periplasmic chaperone protein), the PapG adhesin protein complexed with its chaperone protein PapD or the full-length FimH adhesin protein (alone or complexed with FimC). Of course, any adhesin assembled by the chaperone/usher pathway could be prepared and utilized as a vaccine according to the present invention.

In another aspect of the invention, such an immunogenic composition may be utilized to produce antibodies to diagnose urinary tract infections, or to produce vaccines for prophylaxis and/or treatment of such infections as well as booster vaccines to maintain a high titer of antibodies against the immunogen(s) of the immunogenic composition.

While other antigens have been utilized to produce antibodies for diagnosis and for the prophylaxis and/or treatment of bacterial urinary tract infections, there is a need for improved or more efficient vaccines. Such vaccines should have an improved or enhanced effect in preventing bacterial infections mediated by adhesins and pili.

There is a need for improved antigenic compositions comprising adhesins for stimulating high-titer specific antisera to provide protection against infection by pathogenic bacteria and also for use as diagnostic reagents.

In one aspect, the present invention is directed to an immunogenic composition comprising a purified complex of a periplasmic chaperone protein and a chaperone-binding protein. The chaperone-binding protein is maintained in the complex in an immunogenic form capable of inducing an immune response when appropriately introduced into a human or other mammalian species. Adhesins are suitable chaperone-binding proteins for use in these immunogenic compositions.

In this specification, the terms "pili", "fimbriae," and "fibrillae" are used to refer to heteropolymeric protein structures located on the extracellular surface of bacteria, most commonly gram-negative bacteria. Typically these structures are anchored in the outer membrane. Throughout this specification the terms pilus, pili, fimbriae, and fibrilla will be used interchangeably.

A "periplasmic chaperone" is defined as a protein localized in the periplasm of bacteria that is capable of forming complexes with a variety of chaperone-binding proteins via recognition of a common binding epitope (or epitopes). Chaperones perform several functions. They serve as templates upon which proteins exported from the bacterial cell into the periplasm fold into their native conformations. Association of the chaperone-binding protein with the chaperone also serves to protect the binding proteins from degradation by proteases localized within the periplasm, increases their solubility in aqueous solution, and leads to their sequentially correct incorporation into an assembling pilus.

According to the present invention, it has been found that FimH or fragments thereof that retain mannose binding capability (alone or complexed with FimC) are superior immunogens to the protein PapG for prevention of bladder infections due to *E. coli*. A superior immunogen is defined as an antigen that will stimulate a greater immune response, or a response that will last longer than the immune response to another antigen utilized in the same immunization protocol, or an antigen that will confer better protection against bladder infections (e.g., FimH, FimC-H or PapD/PapG).

The protein fragments and proteins of the invention are useful immunogens for preparing vaccine compositions that stimulate the production of antibodies that can confer immunity to pathogenic species of bacteria. Further, preparation of vaccines containing purified proteins as antigenic ingredients are well known in the art.

Generally, vaccines are prepared as injectables, in the form of aqueous solutions or suspensions. Vaccines in an oil base are also well known such as for inhaling. Solid forms which are dissolved or suspended prior to use may also be formulated. Pharmaceutical carriers are generally added that are compatible with the active ingredients and acceptable for pharmaceutical use. Examples of such carriers include, but are not limited to, water, saline solutions, dextrose, or glycerol. Combinations of carriers may also be used.

Vaccine compositions may further incorporate additional substances to stabilize pH, or to function as adjuvants, wetting agent, or emulsifying agents, which can serve to improve the effectiveness of the vaccine.

Vaccines are generally formulated for parenteral administration and are injected either subcutaneously or intramuscularly. Such vaccines can also be formulated as suppositories or for oral administration, using methods known in the art.

The amount of vaccine sufficient to confer immunity to pathogenic bacteria is determined by methods well known to those skilled in the art. This quantity will be determined based upon the characteristics of the vaccine recipient and the level of immunity required. Typically, the amount of vaccine to be administered will be determined based upon the judgment of a skilled physician. Where vaccines are administered by subcutaneous or intramuscular injection, a range of 50 to 500 $\mu$g purified protein may be given.

The term "patient in need thereof" refers to a human that is infected with, or likely, to be infected with, pathogenic bacteria that produce pili and/or chaperone-binding proteins, preferably *E. coli* bacteria (however a mouse model can be utilized to simulate such a patient in some circumstances).

In addition to use as vaccines, such pili adhesin proteins, mannose-binding adhesin protein fragments, and complexes of periplasmic chaperone proteins and such pili adhesin proteins can be used as immunogens to stimulate the production of antibodies for use in passive immunotherapy, for use as diagnostic reagents, and for use as reagents in other processes such as affinity chromatography.

In an aspect of the invention complexes comprising the *E. coli* chaperone FimC and the FimH adhesin associated with type 1 pili may be recovered from *E. coli*. These complexes are found in relatively great amounts in recombinant *E. coil* strains which express the FimC protein at levels in excess of those produced in wild type strains. A suitable recombinant strain is C600/pHJ9205, a strain in which expression of FimC has been put under control of the arabinose promoter. Those skilled in the art will recognize that other promoter sequences that can be regulated easily may also be used.

Because FimC is a periplasmic chaperone, proteins isolated from the periplasm of *E. coli* serve as the starting material for the purification. An extract of periplasm is obtained by exposing the bacteria to lysozyme in the presence of a hypertonic sucrose solution. The elution of periplasmic proteins so obtained are separated from cellular proteins by centrifugation.

The FimC-H complexes are purified from the crude mixture of periplasmic proteins. One method for achieving this purification takes advantage of the affinity of the FimH adhesin for D-mannose residues. Because of this affinity, FimC-H complexes will bind to mannose which has been covalently attached to a suitable chromatography resin, such as Sepharose. After binding reaches equilibrium the beads are washed to remove unbound, contaminating proteins. Bound FimC-H complexes may then be eluted from the beads using a solution containing mannose-residues, such as, for example. methyl-α-d-mannopyranoside. To achieve further purification of the complexes, an additional chromatography step, such as ion exchange chromatography, may be used. Alternatively, FimC-H complexes can be purified using conventional protein purification methods.

In a similar manner, FimH fragments that are recombinantly produced either by having *E. coli* produce the full-length FimH protein and then fragmenting the protein or are produced recombinantly may be isolated by the above mannose-binding affinity purification. Thus, only fragments of the FimH protein that retain mannose binding are isolated. Preferably, the mannose-binding fragments have a label such as a his-tag included and may be purified by methods such as Nickel chromantography (see examples below).

The present invention provides for a recombinant production or synthesis of adhesin proteins of pilus-bearing bacteria adhesin proteins in the presence or absence of its chaperone protein for use as a vaccine (or as an immunogen to produce antibodies for diagnostic or therapeutic purposes). In particular an adhesin protein may be individually expressed or co-expressed with its corresponding periplasmic chaperone protein to make a complex of the co-expressed proteins. Preferably, the adhesin protein is a substantially full-length FimH protein, or an analog or derivative thereof which maintains mannose binding capability. In this regard cDNA, RNA and genomic sequences for such chaperone and adhesin proteins are known. See Tables 1 and 2, below.

Moreover, the known sequences of chaperone and adhesin proteins as referred to in Tables 1 and 2 may be utilized as probes to retrieve other polynucleotides (such as from other species) that encode the same or similar proteins which polynucleotides may then be utilized for such recombinant expression. For example, it is well-known in the art that FimH is highly conserved among various bacterial species (not just among *E. coli*).

Tables 1 and 2 are as follows:

TABLE 1

BACTERIAL CHAPERONE PROTEINS AND THEIR SOURCE

| Chaperone Protein | Gen Bank Accession No. | Organism |
|---|---|---|
| PapD | X61239 | *E. coli* |
| FaeE | X56003 | *E. coli* |
| FanE | X56001 | *E. coli* |
| Sfae | 227911 | *E. coli* |
| MrkB | M55912 | *K. pneumonia* |
| HifB | X66606 | *H. influenzae* |
| FimC | Z37500 | *E. coli* |
| MrpD | Z32686 | *P. mirabilis* |
| FocC | Z46635 | *E. coli* |
| FimB | X64876 | *B. pertussis* |
| PefD | L08613 | *S. typhimurium* |
| PmfD | Z35428 | *P. mirabilis* |
| LpfB | U18559 | *S. typhimurium* |
| FasB | U50547 | *E. coli* |
| HafB | U54780 | *H. influenzae* |
| AftB | L77091 | *P. mirabilis* |
| F17D | AF022140 | *E. coli* |
| EcpD | L00680 | *E. coli* |
| YehC | AE000300 | ? |

TABLE 1-continued

BACTERIAL CHAPERONE PROTEINS AND THEIR SOURCE

| Chaperone Protein | Gen Bank Accession No. | Organism |
|---|---|---|
| YraI | AE000395 | *E. coli* |
| RalE | U84144 | Rabbit EPEC |
| ClpE | L05180 | *E. coli* |
| CssC | U04844 | *E. coli* |
| MyfB | Z21953 | *Y. enterocolitica* |
| PsaB | M86713 | *Y. pestis* |
| CS3-1 | X16944 | *E. Coli* |
| CaflM | X61996 | *Y. pestis* |
| NfaE | S61968 | *E. coli* |
| SefB | L11009 | *S. enteritidis* |
| AggD | U12894 | *E. coli* |
| AfaB | X76688 | *E. coli* |

TABLE 2

BACTERIAL ADHESIN PROTEINS AND THEIR SOURCE

| Adhesin Protein | Accession No. | Organism |
|---|---|---|
| PagG | 42391 | *Escherichia coli* |
| PrsG | 1172645 | *Escherichia coli* |
| SfaS | 134449 | *Escherichia coli* |
| FimH | 1361011 | *Escherichia coli* |
| HifE | 642038 | *Haemophilus influenza* |
| HifE | 1170264 | *Haemophilus influenza* |
| FocH | 239711 | *Escherichia coli* |
| FimD | 480043 | *Bordetella pertussis* |
| FimD | 416479 | *Bordetella bronchiseptica* BB171 |
| PmfE | 1709671 | *Proteus mirabalis* |
| LpfD | 1361301 | *Salmonella typhimurium* |

The chaperone and adhesin proteins as well as the sources for their genes (or cDNA) are listed in the above tables for illustrative purposes only. For example, the polynucleotides encoding FimH, FimC-H complex and FimH mannose-binding fragments may vary and the encoded proteins also vary from organism to organism and from species to species. While the FimH protein is highly conserved across different species (e.g., *E. coli*, Salmonella and Klebsiella) and in various strains of *E. coli*, the amino acid sequences of FimH do vary to some extent. However, such variant amino acid sequences (as well as their analogs and mannose-binding fragments) are contemplated within the meaning of the terms "FimH" and "a FimH mannose-binding fragment" when such terms are utilized in this application, for example. The meanings of such terms are not limited to the particular amino acid sequences shown or to the particular species of *E. coli* specifically described in the specification or utilized in the examples.

The polynucleotides encoding the proteins above and in the above tables may also have the coding sequence fused in frame to a marker sequence which allows for purification of the polypeptides of the present invention. The marker sequence may be, for example, a hexa-histidine tag supplied by a pQE-9 vector to provide for purification of the mature polypeptides fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

In a preferred aspect, the invention provides for recombinant production of such proteins, chaperone/adhesin complexes and mannose-binding fragments of such proteins in an *E. coli* species host. A preferred host is a species of such bacteria that can be cultured under conditions such that the usher gene (if present) is not expressed. Further preferred is a host species that is missing the usher gene or has a defective usher gene. Even further preferred is a host which is missing the pilus proteins other than the adhesin protein (and preferably produces its chaperone). When an adhesin protein or a mannose binding fragment of such adhesin protein is to be produced in the absence of its chaperone protein (or to be separated from the chaperone after production), the adhesin protein (or fragment) may be permitted to become properly folded in the presence of its chaperone protein and is then separated from the chaperone protein.

The present invention also relates to vectors which include polynucleotides encoding one or more of the adhesin or chaperone proteins of the present invention, host cells which are genetically engineered with vectors of the invention and the production of such adhesin proteins and/or chaperone proteins by recombinant techniques in an isolate and substantially immunogenically pure form.

Host cells are genetically engineered (transduced or transformed or transfected) with the vectors comprising a polynucleotide encoding a chaperone, adhesin protein, mannose binding fragment of an adhesin protein, or the like of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the polynucleotides which encode such polypeptides. The culture conditions, such as temperature, pH and the like, are those previously used with the host cell selected for expression, and will be apparent to the ordinarily skilled artisan.

Vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli*. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

In accordance with the present invention, optimal expression of a FimH-C complex has been achieved using a newly constructed single vector containing the FimH and FimC genes but having the advantage that each gene is under its own separate lac promoter. Thus, one lac promoter is 5' with respect to FimC while the second lac promoter is 5' to the FimH gene. This plasmid was successfully constructed using the common plasmid pUC19 as a background vector [Yannish-Perron, C., Vierira, J. and Messing, J., Gene, 33:103–119 (1985)]. This new plasmid, when used to transform the host *E. coli* strain BL21 [as described in Phillips, T. A., Van Bogelen, R. A., and Neidhart, F. C., J. Bacteriol. 159:283–287 (1984)] and then induced using IPTG at the mid-logarithmic stage of growth, gives maximal expression of the FimCH complex in the bacterial periplasmic space. This material is then extracted and purified by methods well known in the art, including those described herein.

The vector containing the appropriate DNA sequence as hereinabove described, as well as an appropriate promoter or control sequence, may be employed to transform an appropriate host to permit the host to express the proteins.

As representative examples of appropriate hosts, there may be mentioned: bacterial cells, such as *E. coli, Streptomyces, Salmonella typhimurium*; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen, Inc.), pbs, pD10, phagescript, psiX174, pbluescript SK, pbsks, pNH8, pNH16a, pNH18, pNH46 (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $PR_R$, $P_L$ and TRP. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, a french press, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides can be recovered and/or purified from recombinant cell cultures by well-known protein recovery and purification methods. Such methodology may include ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. In this respect, chaperones may be used in such a refolding procedure. Finally, high performance liquid chromatography (HPLC) can be employed for final purification steps.

The polypeptides that are useful as immunogens in the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Particularly preferred immunogens are FimH adhesin protein or mannose-binding fragments thereof since FimH is highly conserved among many bacterial species. Therefore, antibodies against FimH (or its mannose-binding fragments) should bind to FimH of other bacterial species (in addition to *E. coli*) and vaccines against *E. coli* FimH (or FimH mannose-binding fragments) should give protection against other bacterial infections in addition to *E. coli* infections (for example, against other enterobacteriacea infections).

Procedures for the isolation of a periplasmic chaperone protein complexed with an adhesin protein are known in the art, as an example see Jones et al., Proc. Natl. Acad. Sci. (USA) 90:8397–8401 (1993). Further, the individually expressed adhesin proteins may be isolated by recombinant expression/isolation methods that are well-known in the art. Typical examples for such isolation may utilize an antibody to the protein or to a His tag or cleavable leader or tail that is expressing as part of the protein structure.

The polypeptides, their fragments or other derivatives, or analogs thereof, or cells expressing them can be used as an immunogen to produce antibodies thereto. These antibodies can be, for example, polyclonal or monoclonal antibodies.

The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a non-human. The antibody so obtained will then bind the polypeptides itself. In this manner, even a sequence encoding only a fragment of the polypeptides can be used to generate antibodies binding the whole native polypeptides.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

In order to facilitate understanding of the above description and the examples which follow below certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 pg of approximately equimolar amounts of the DNA fragments to be ligated.

"FimHt" in the mouse in vivo experiments below refers to a naturally occurring FimH adhesin protein truncate corresponding to the $NH_2$-terminal two-thirds of the FimH protein which was purified away from complexes of FimC and FimH (FimC-H)). Such FimHt has mannose-binding capability. However, in other locations in the specification and FIGS., the terms "FimHt" or "FimH truncate" may refer to either a naturally occurring protein truncate having mannose-binding capability or to a labelled (such as His-tag) or unlabelled recombinant fragment of FimH that has mannose-binding capability.

Unless otherwise stated, transformation was performed as described in the method of Graham, F. and Van der Eb, A., Virology, 52:456–457 (1973).

The present invention will be further described with reference to the following examples; however, it is to be understood that the present invention is not limited to such examples. All parts or amounts, unless otherwise specified, are by weight.

EXAMPLE 1

Immunogenicity of Adhesin, Adhesin/Chaperone and Whole Pili

The immunogenicity of purified adhesin, adhesin-chaperone complex or whole type 1 pili proteins were assessed by measuring immunoglobulin G (IgG) titer to FimHt adhesin (a naturally occurring FimH truncate corresponding to the $NH_2$ terminal two-thirds of the FimH protein which was purified away from complexes of FimC and FimH (FimC-H)) and whole type 1 pili, respectively, up to 78 weeks post immunization.

C3H/HeJ mice, five mice per group were immunized on day 0 (primary immunization) [in Freund's adjuvant (CFA)] and booster immunization (week 4) [in incomplete Freund's adjuvant (IFA)] with one of the three antigens: purified adhesin (FimHt), adhesin-chaperone complex (FimC-H) or whole type 1 pili. Samples from individual mice treated identically were pooled for serological analysis and diluted 1:100 before serial dilution. Antibody responses were assessed by an ELISA with purified FimHt or whole pili as the capture antigens. Titers reflect the highest dilution of serum reacting twice as strongly as a comparable dilution of preimmune sera obtained from the same mice. The purity of the protein preparations of the capture antigens was 95% pure for whole type 1 pili and FimHt to 98 to 99% purity for FimC-H. In all cases the protein preparations were free of any lipopolysaccharide contaminants. Data for immune responses of such mice to FimHt adhesin (FIG. 1). and whole type 1 pili (FIG. 1B) of such mice are reported in FIGS. 1 and 1B as FimHt (squares), FimC-H (circles) or whole type 1 pili (triangles).

Figure 1B:
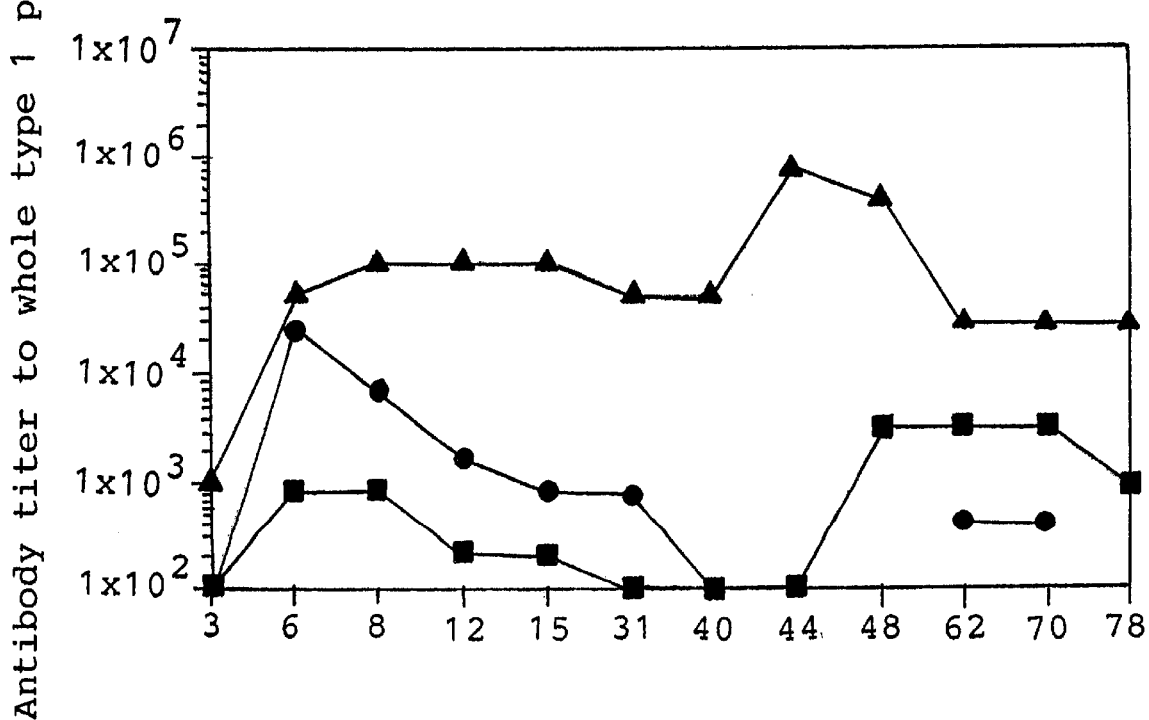

As shown in FIGS. 1 and 1B, both FimHt and FimC-H induced strong, long-lasting immune responses to isolated FimHt and to FimH associated with whole type 1-pilus organelles. The responses persisted more than 30 weeks, and booster immunizations with FimHt or FimC-H increased responsiveness. In contrast, type 1 pili elicited poor anti-FimH responses even though mice developed strong responses to whole pilus rods. Immunization studies in rabbits demonstrated similar immunogenicity profiles to those seen in mice. Antisera to FimHt and to FimC-H bound to recombinant type 1+/FimH+ E. coli strains (ORN103/pSH2) but not to the type 1+/FimH− isogeneic mutant (ORN103/pUT2002) as determined by indirect immunofluorescence and flow cytometric analysis. Antibody to the whole pilus bound both ORN103/pSH2 and ORN103/pUT2002, as expected.

Comparable immune responses (unreported) to the three antigens FimHt, FimC-H and whole type 1 pili were seen in BALB/C and C57/BL6 strains of mice.

EXAMPLE 2

Role of FimH in E. coli Binding Human Bladder Cells

The ability type 1-piliated *E. coli* to bind to human and mouse epithelial tissues was investigated in the absence and presence of FimH. The presence of a receptor for binding of type 1 pili to human bladder mucosa that is recognized by FimH was verified by determination of superior binding results when the FimH protein is present. FimH is the adhesin that confers mannose-specific binding activity to type 1 pili since adding mannose results in the inhibition of such binding.

In situ binding of *E. coli* to human and mouse tissues elucidates the binding role of FimH in the adhesin of type 1 pili to such tissues. A NU14 *E. coli* (serotype) cystitis isolate from UTI patents bound to the luminal surface of both mouse and human bladder epithelium. However, the presence of mannose completely blocked this binding.

Tests were then performed to determine that FimH is responsible for such binding. A mutant form of *E. coli* was provided that did not produce FimH protein. A chloramphenicol cassette recombined with the fimH gene in the chromosome of strain NU14 creates a fimH- mutant NU14–1 (i.e., bacteria that does not produce FimH). Binding assays confirm that such mutant fails to bind the human and mouse bladder tissues while the wild type bacteria maintains the ability to bind such tissues. Further the mutant can then be modified further genetically to provide regulated restoration of such gene and its expression restored the ability of the bacterial pili to bind to the human and mouse bladder walls.

Thus, FimH is responsible for the adhesin binding of type 1 pili to bladder epithelial cells. According, antibodies to such protein should block the binding of type 1 pili to such cells and result in prevention or treatment of UTIs that are caused by type 1-piliated *E. coli*.

EXAMPLE 3

Standard Ability of E. coli to Bind Human Bladder Cells

The ability of type 1-piliated *E. coli* to bind to human bladder cells epithelial cells was investigated in vitro by a flow cytometric method modified from a procedure originally developed to evaluate Rickettsia-cell attachment. In vitro binding of type 1-piliated *E. coli* to human bladder (J-82 (ATCC HTB1) in the absence of anti-binding antibodies was assayed to obtain standard binding rates for particular bacteria.

The ability of Type 1-piliated *E. coli* of HB101/pSH2 (and strain ORN103/pSH2) and *E. coli* NU14 to bind to bladder cells from the human bladder epithelial cell line J82 was measured as follows.

Type 1-piliated, NU14 and nonpiliated [HB 101 (cross-hatched)] bacteria were directly labeled with FITC and tested for their ability to bind to bladder cells. The labelled bacteria were first assayed for the expression of type 1 pili. Such expression of type 1 pili was confirmed by hemagglutination of a 3% solution of guinea pig erythrocytes and inhabitation of hemagglutination by a 10 mM solution of α-methylmannoside.

Next the labeled bacteria were incubated with $2\times10^6$ J82 (ATCC HTB1) bladder cells at the bacteria:bladder cell concentration ratios of 1000:1 to 62.5:1. Samples were assayed by flow cytometry in a FACStar PLUS (Becton Dickinson). Mean channel fluorescence was used as an indicator of FITC-labeled bacteria bound for J82 cells. The threshold for positivity was set for each experiment by flow cytometric analysis of J82 cells that were incubated with PBS only. For evaluation of FITC labeling of bacteria, gates were set with non-FITC-labeled bacteria. Lysis II software (Becton Dickinson immunocytometry Systems) was used for analysis of data.

FIG. 2 shows the bladder cell binding results for such type 1-piliated [HB101/pSH2 (black bars) and NU14 (striped bars)] and nonpiliated [HB 101 (cross-hatched)] bacteria.

EXAMPLE 4

Ability of Antibodies to Inhibit Binding of E. coli Species to Human Bladder Cells The ability of anti-FimHt antibodies to inhibit the binding of type 1-piliated *E. coli* to human bladder cells epithelial cells was investigated in vitro by the flow cytometric method described in Example 2. In vitro binding of type 1-pilated *E. coli* to human bladder (J-82 (ATCC HTB1) in the presence of anti-FimHt antibodies was assayed for as set forth below.

High titer anti-FimHt or anti-FimC-H antibodies were obtained as antisera from bleeds of mice at 6 to 9 weeks post initial immunization as set forth in Example 1. About $2.5\times10^8$ HB101/pSH2 or NU 14 bacteria incubated for 30 min at 37° C. with such high-titer anti-FimHt or anti-FimC-H (from bleeds at 6 to 9 weeks) at 1:50, 1:100, or 1:200 dilutions in PBS or with PBS alone. After incubation with the antisera, $2\times10^8$ J82 cells were added and allowed to mix with the bacteria for 30 min. at 37° C. The remainder of the adherence assay and evaluation by flow cytometry were carried out as described in Example 3. J82 bladder cells that were sorted from the flow cytometric adherence assay were also analyzed by fluorescent microscopy. The number of fluorescent bacteria attached to 40 bladder cells was visually quantitated. Adherence values (mean number of bacteria±SD per cell) for two representative cystitis isolates, NU14 and EC72, were 35.2±4.9 bacteria/cell, respectively, in the absence of FimH-specific antibody; incubation with a 1:50 dilution of anti-FimH-specific antibody; incubation with a 1:50 dilution of anti-FimH completely blocked attachment. Furthermore, the same examination of samples taken from bacteria incubated with different dilutions of anti-FimHt confirmed the dose-dependency of the phenomenon.

Figure 2A:
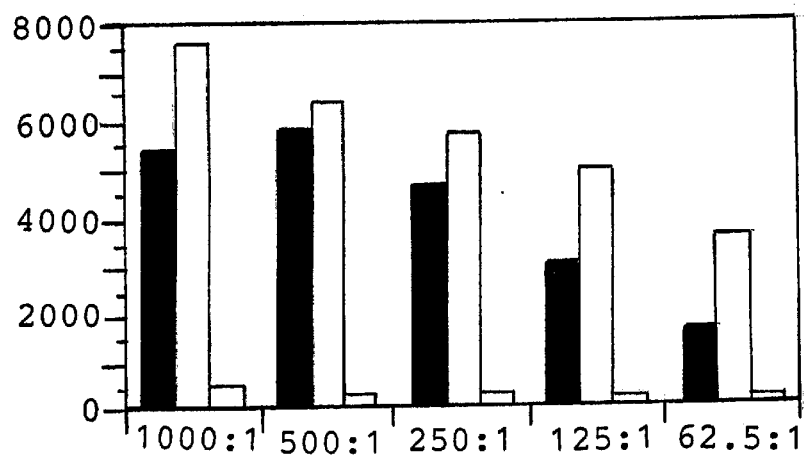
FIGS. 2A–2C report the data for in vitro binding of type 1-piliated *E. coli* to human bladder epithelial cells and inhibition by anti-FimH.
Figure 2B:
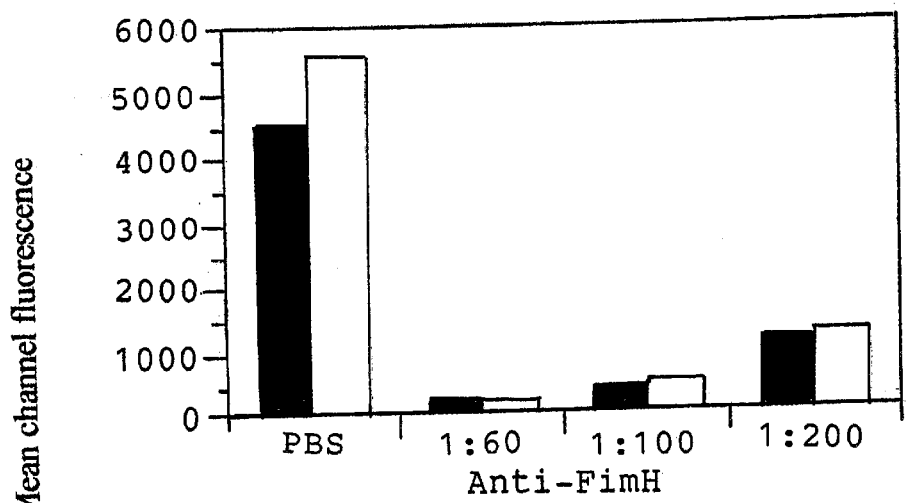
Figure 2C:
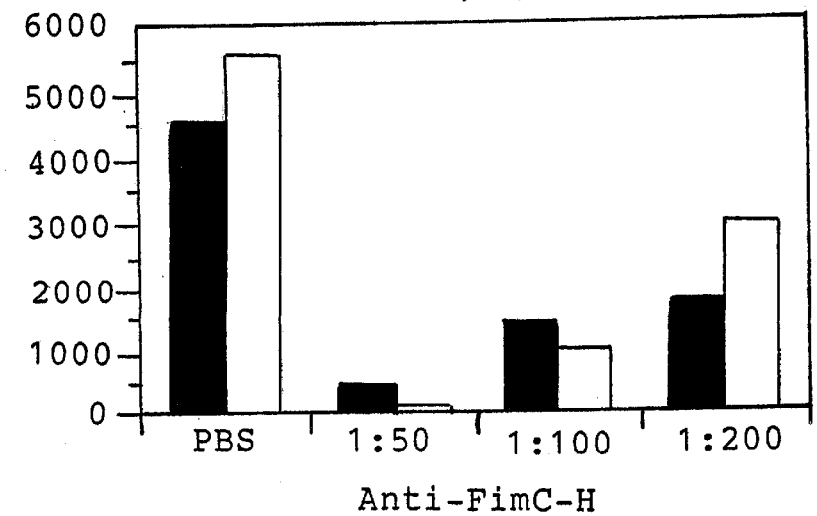

The abilities of the anti-FimHt and anti-FimC-H antibodies (antibodies to the truncated adhesin protein and to the adhesin protein FimH complexed with its chaperone FimC, respectively) to prevent bacterial binding to such bladder cells are set forth in FIGS. 2B and 2C, respectively.

At the antibody dilutions 1:50, 1:100 and 1:200 in PBS each of the antibody (antisera) dilutions strongly inhibited the ability of type 1 piliated bacteria to bind to the human bladder cells as verified by the PBS control solution which had no antibodies present.

EXAMPLE 5

Effects of Antibody Titer on Antibody Inhibition of E. coli Species Binding to Human Bladder Cells The procedures for antibody inhibition of bacterial binding as set forth in Example 4 were followed except that the antibodies to FimHt and FimC-H were obtained at various time periods and at various titer levels as set forth in Example 1.

The results observed (not shown) establish that there is a direct relationship between the antibody titer to FimH and the ability of the antisera to block microbial attachment (functional inhibitory titer). Furthermore, as titer to FimH dropped or levelled off in the FimHt-immunized and FimCH-immunized mice, the concomitant functional inhibitory titers dropped as well. However, as titers increased after a booster immunization at week 42, the corresponding functional inhibitory titers were elevated.

Utilizing such results (not shown), the functional inhibitory titers of anti-FimHt was determined for a panel of primary clinical isolates from women and children with active urinary tract infections. Antisera raised to FimHt and FimC-H blocked attachment of 49 out of 52 (roughly 94%) primary clinical E. coli UTI isolates induced to express type 1 pili (results not shown). A subset of strains induced to express P pili, S pili, or both in addition to type 1 pili were also inhibited from attachment to the bladder epithelial cells by anti-FimHt antibodies.

EXAMPLE 6

(Comparative Example)

Effects of Antibodies to Whole Type 1 Pili Inhibition of E. coli Species Binding to Human Bladder Cells The antibody inhibition of bacteria binding procedures of Example 5 were followed with antibodies to whole type 1 pili (obtained as set forth in Example 1), in purified form ORN103/pSH2, were poor inhibitors of bacterial binding to bladder epithelial cells; antisera to whole type 1 pili blocked<50% of the clinical isolates even at a 1:50 dilution of antiserum. Such is presumably due to the variation in antigenicity of FimA among clinical isolates and the inability of whole type 1 pili to elicit significant anti-FimH responses. Preimmune sera and antisera from mice given adjuvant alone or antisera from mice immunized with a control FimC chaperone protein did not inhibit binding.

EXAMPLE 7

Immunization Effects of FimnH and FimC-H to Inhibit E. coli Species Binding in Mouse Bladder A C3H/HaJ murine cystitis model was utilized to demonstrate the effectiveness of immunization with a FimHt or FimC-H vaccine (see generally the immunization procedures in Example 1, above).

As a control to assess UTI levels in the bladders of unprotected mice, ten to 15 week old C3H/HeJ mice were anesthetized with methoxyflurane and challenged with various doses of streptomycin-resistant, type 1-piliated E. coli NU14 (an isolate from a clinical human UTI). The values that were measured represent the final challenge doses the mice received of the NU14. The colony-forming units per bladder that are measured represent the mean ± SD for each group (N=10, group of ten mice) 2 days after the challenge with NU14.

Figure 3A:
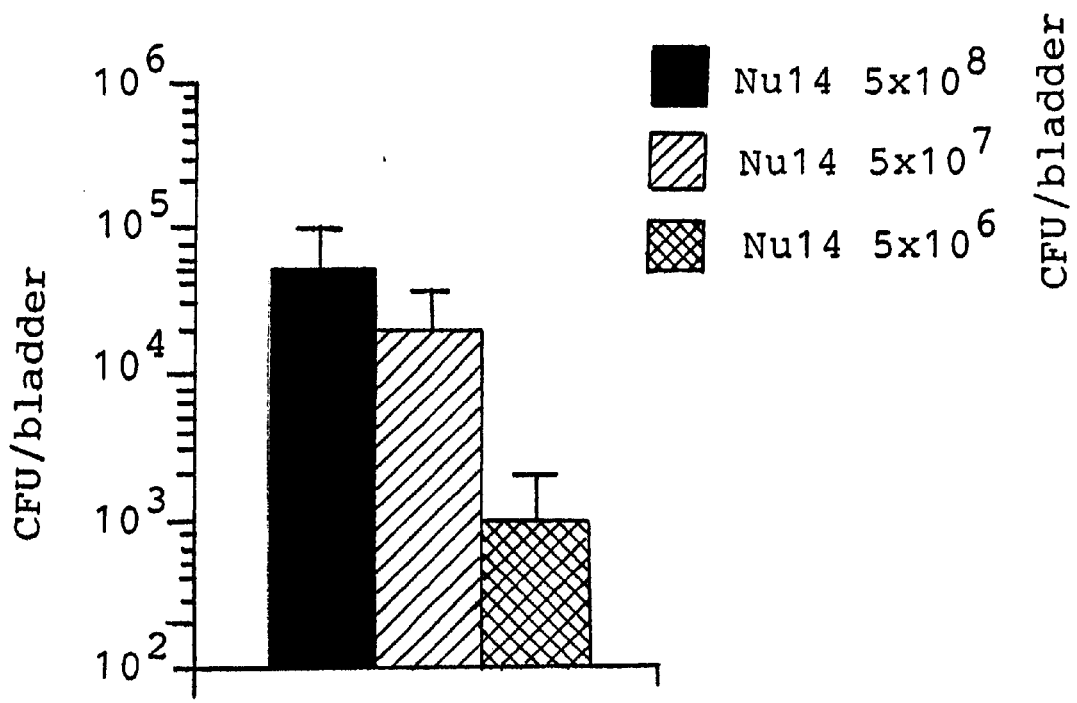

Intraurethral inoculation of C3 H mice with $5 \times 10^7$ type 1-piliated E. coli (strain NU14) resulted in a highly reproducible colonization of the mouse bladder in unvaccinated mice (See FIG. 3A). Piliated bacteria persisted in the bladder for at least 7 days [$10^4$ colony-forming units (CFU)/bladder] and produced ascending infection into the kidney.

The role of mannose-binding type 1 pili in bladder colonization was investigated by testing the effect of the fimH- mutation (see Example 2, above) as compared to the fimH+wild-type in the murine model. Ten to 15-week old C3 H/HeJ mice were anesthetized and challenged with $10^7$ and $10^5$ CFU of either E. coli NU14 (type 1+/FimH+) or NU14–1(fimH–). The data measured represents the mean ± SD for each group (N=10, group of ten mice) 2 days variance was used in the calculation as well as the Dunnet's t test for multiple comparisons. Inoculation with the fimH-mutant, NU14–1, resulted in little or no colonization of the mouse bladder (FIG. 3B), supporting the indication in Example 2 (above) that FimH plays a critical role in colonization of the bladder.

The protective effects against E. coli bladder infections in immunized mice provided by in vivo anti-FimHt and anti-FimC-H (mice immunized with FimHt and FimC-H as set forth in Example 1) as contrasted with in vivo anti-FimC (mice immunized with FimC alone by following the procedures and protocol as set forth in Example 1) were assayed for as follows.

Four groups of C3 H/HeJ mice were immunized on day 0 and boosted at week 4 with purified FimHt protein (doses ranging from 0.6 to 30 μg in CFA for the initial immunization and IFA for the booster), FimC or the adjuvant alone, as generally set forth in Example 1. At week (9) nine after immunization (high titer, see Example 1 data reported in FIG. 1A) the urine of the immunized mice was assayed for the presence or absence of the antibody corresponding to the immunization. Mice that received the FimHt vaccine had significant amounts of IgG to FimHt in their urine, whereas unimmunized mice, or mice vaccinated with FimC alone, did not have any measurable amounts of anti-FimHt in urinary secretions.

The protective effects of such in vivo antibodies resulting from such vaccination were assessed concurrently with the measurement of antibodies in the urinary secretions as set forth below. Such assessment is helpful in determining the effectiveness of such vaccine for the prevention of UTIs.

The average number of colony-forming units per bladder for each group of 10 mice was evaluated in the same manner as indicated for the control group of unprotected mice above. FimC-immunized mice were also included as a negative control along with naive mice. [P - 0.0001 comparing the 30-, 15 and 3-μg doses of FimHt with the naive data; P=0.205 for the FimC negative control at the highest (30 μg) dose].

The C3H mice that were immunized with the various vaccines as set forth above were challenged with $5 \times 10^7$ CFU of type 1-piliated E. coli (NU14 isolate, see above) at week 9 after immunization (high titer, see Example 1 data reported in FIG. 1A). Animals vaccinated with FimHt exhibited from a 100- to 1000-fold reduction in the number of organisms recovered from the bladders as compared with the control mice that were immunized with only adjuvant or with only FimC. The CFUs for such mice are set forth in FIG. 3C. Protection with the FimHt vaccine was seen as late as 29 weeks after immunization, the latest time point tested. Such mice were provided with additional vaccination at 51 weeks and rechallenged at 54 weeks. Protection was also seen at such 54 week period.

The above procedures were repeated with FimC-H as the vaccine instead of FimHt. Similar protective results were seen with the FimC-H vaccine (not reported) as were observed for FimHt at 29 weeks. Such mice were provided with additional vaccination at 51 weeks and rechallenged at 54 weeks. Protection was also seen at such 54 week period.

To access the in vivo protective effects against ascending UTI infections in the mouse model, the above immunization procedures were repeated with two groups of C3H/HeJ mice. Such mice were inoculated on day 0 with 15 μg CFA and boosted at week 4 with purified FimHt protein (15 μg IFA) or with CFA/IFA adjuvant alone. At week 9 post immunization the presence of antibodies was assessed by the above described urine test. At the time of such urine test the mice were challenged with $5 \times 10^7$ CFU of type 1-piliated $E.$ $coli$ strain.

The average number of CFUs were assessed as set forth above, except that the CFUs were assessed per kidney (instead of per bladder) for each group of 10 challenged mice. The average number of CFUs was evaluated as indicated above 7 days after the intraurethral challenger (P=0.295) (see FIG. 3D, where solid histogram is mice administered anti-FimHt and cross-hatched histogram is naive mice). Such data indicates that such vaccination blocked an ascending infection into the kidney over a 7-day period.

EXAMPLE 8

Protective Effects of Antibody Sera in Non-immunized Mice For Inhibiting $E.$ $coli$ Binding in Mouse Bladder To confirm the protective effects that were observed in Example 7 were mediated by anti-FimHt, naive C3 H mice were challenged with $5 \times 10^7$ type 1-piliated $E.$ $coli$ strain NU14 after passive, intraperitoneal administration of hyperimune mouse FimHt antisera (or FimC-H antisera) raised to either the FimHt protein or the FimC-H complex. In each cases the sera containing anti-FimHt or anti FimC-H resulted in a 100- to 150-fold reduction in the number of organisms recovered from the bladder 2 days after challenge (See FIG. 3E). Sera from mice that received only adjuvant did not have any protective effects at all against such bladder infections or ascending UTIs.

EXAMPLE 9

Protective Effects in FimH and FimC-H Immunized Neutropenic Mice Against $E.$ $coli$ UTIs in Mouse Model Non-immunized and FimH-immunized mice were rendered neutropenic before intraurethral challenge with type 1-piliated $E.$ $coli$ to determine whether protection was neutrophil dependent. The assays for the number of organisms in the mice bladders were determined as set forth above in Example 8.

As control groups, mice that were nonimmunized and neutropenic showed a 100-fold increase in the number of organisms in the bladder relative to immunocompetent, nonimmunized mice ($10^6$ CFU/bladder compared with $10^4$ CFU/bladder).

Immunization with FimH vaccine reduced colonization in both neutropenic and non-neutropenic mice to equivalent levels of $10^2$ CFU/bladder. Thus, the absence of neutrophils did not impede the antibacterial activities of the FimH vaccine in vivo.

EXAMPLE 10

Recombinant Expression and Purification of FimCH By Cation and Hydrophobic Interaction Chromatography Polynucleotides encoding FimC (in a plasmid vector with an arabinose promoter and spectinomycin resistance; obtained by inserting an FimC gene into a plasmid vector such as are commercially available) and FimH (pHJ20-FimH-pMMB66; IPTG promoter and ampicillin resistance; FimH gene inserted into a commercially available plasmid vector by standard techniques, equivalents are readily available), respectively, were inserted into an $E.$ $coli$ strain (C600/pHJ9205/pHJ20) under standard calcium chloride conditions. A stock culture of the $E.$ $coli$ strain with its inserts was then obtained for use as a fermentation inoculate.

The $E.$ $coli$ host cells of the stock culture were grown under conditions such that the type 1 usher protein was not expressed. In particular, 16 liters of media (11 liters LB Millers and 5 liters BHI; commercially available) was autoclaved and placed in a 20 liter fermentor (New Brunswick Bioflow IV). Culturing conditions of the fermentor are a constant temperature of 37° C., pH 7.4, agitation 500 rpm and $DO_2$ 90%–25%. The media was inoculated with 500 ml of stock culture to provide a starting optical density (O.D.) of 0.1. At about 2–3 hours and an O.D. of 0.6, 0.2% arabinose was added. Then at an O.D. of 1.2, 0.25 mM IPTG was added.

After the IPTG was added, the culture was maintained for about 1 hour and the $E.$ $coli$ host cells were harvested in CEPA LE continuous flow centrifuge. The dry weight of the pellet was a yield of about 100–150 grams of cells.

The pellet was placed in a container on ice and to prepare the periplasm there was added per gram of cells: 4 ml 20% sucrose/20 mM Tris 8.0; 200 μl EDTA 8.0; and 40 μl lysozyme (10 mg/ml). After such addition the mixture was maintained on ice for about 20 minutes. Then 160 μl of 0.5 M $MgCl_2$ was added to the mixture and the mixture was centrifuged at 12,000 g. The supernatant was brought to 75% $NH_4SO_4$ and then centrifuged for at least 2 hours (preferably overnight). The $NH_4SO_4$ pellet was then centrifuged at 12,000 g for 30 minutes and dialyzed against 20 mM KMES pH 6.8.

FimCH was purified by chromatography, cation exchange chromatography followed by hydrophobic interaction chromatography. A sample obtained by the above procedures was injected on Pharmacia XK16/10 15S Source Sepharose Column at a rate of 2 ml/min, A: 20 mM KMES pH6.8 B: 20 mM KMES 6.8/0.6 M NaCl. The run gradient was 0–30% over 100 ml, 30–100% over 20 ml. The FimCH was eluted at around 60 mM NaCL, and FimC was eluted at around 75 mM NaCl. The respective fractions were pooled from individual runs and then further purified by dialysis into 50 mM NaPhosphate pH7.0/0.6 M $NH_4SO_4$. The FimCH thus obtained was then further purified by hydrophobic interaction chromatography by injecting samples on to Pharmacia HR10/10 Butyl Sepharose 4FF Column at a rate of 2 milliliters per minute: A: 50 mM NaPhosphate pH7.0/0.6M $NH_4SO_4$, and B: 50 mM Naphosphate pH7.0. FimCH was eluted from 180–300 mM $NH_4SO_4$ and dialyzed back to 20 mM KMES pH6.8. The yields from such procedure were an average of 26 mg FimCH per 50 liters.

EXAMPLE 11

Recombinant Expression and Purification of FimCH and FimHt By Affinity and Cation Exchange Chromatography The fermentation and periplasm preparation with the *E. coli* host cells of Example 10 were conducted essentially as set forth in Example 10 except that the $NH_4SO_4$ pellet was centrifuged at 12,000 g for 30 minutes and dialyzed against 1×PBS fully.

Affinity chromatography was utilized to separate a mixture of FimCH and FimHt from the filtered dialysate. In particular, mannose-sepharose beads were added to the filtered dialysate at 1:25 by volume followed by rocking for at least two hours (preferably overnight) in a 50 ml conical tube. The mixture was then centrifuged at 2000 g with no brake and the supernatant was pulled off. This was repeated with 5×washing with 1×pBS. Then one volume of 15% methyl-α-D-mannopyranoside was added and rocked at 4° C. for at least two hours (preferably overnight). The mixture was gently spun by centrifugation and the supernatant containing both the FimCH and FimHt as a mixture was pulled off and dialyzed into 20 mM KMES pH 6.5. The FimCH and FimHt were then separated from one another by cation exchange chromatography of the dialyzate. Samples of the dialyzate were injected onto a Pharmacia XK16/10 15S Source Sepharose Column at a rate of 2 milliliters per minute; A: 20 mM KMES pH6.8 B: 20 mM KMES 6.8/1M NaCl. The FimHt was collected in the flow through at a run gradient of 0–30% over 100 ml, 30–100% over 20 ml. The FimCH was eluted around 100 mM NaCl. Further processing of the respective FimHt and FimCH was done by a final dialysis into 20 mM HEPES 7.0 for crystallography and assays. The yield was an average of 5 mg/50 liters.

EXAMPLE 12

Recombinant Expression and Purification of His-tag FimH Truncates by Nickel and Anion/Cation Chromatography A polynucleotides encoding either FimH or a fragment of FimH (cloned into pMMB91 plasmid as EcoRI/BamHI with IPTG promoter, His-tag and Kanamycin resistance; commercially available plasmid vector, other readily obtainable functionally equivalent vectors may also be used) was inserted into an *E. coli* strain HB101 (commercially available) under standard calcium chloride conditions. Such host cells were designated as HB101/T1–T7 (depending upon the polynucleotide inserted into the *E. coli* strain) and lack an usher protein, thus not needing a chaperone protein except in the case of T7 which is the full-length FimH and may need to have FimC also inserted for proper folding. A stock culture of each *E. coli* strain with its insert was then obtained for use as a fermentation inoculate.

The His-tag FimH truncates and His-tag full-length FimH are as follows: FimHt1(T1=SEQ ID NO:2, amino acids 1 to 161), FimHt2 (T2=SEQ ID NO:2, amino acids 1 to 181), FimHt3 (T3 =SEQ ID NO:2, amino acids 1 to 186), FimHt4 (T4=SEQ ID NO:2, amino acids 1 to 196), FimHt5 (T5= SEQ ID NO:2, amino acids 1 to 207) and FimHt6 (T6=SEQ ID NO:2, amino acids 1 to 223), and FimHt7 (T7=SEQ ID NO:2, amino acids 1 to 300, also referred to as full-length FimH, and encoded by residues 1–900 of SEQ ID NO.: 1) are all produced by the procedures set forth below. For illustrative purposes T2, T3, T4 and T5 were produced as follows.

The *E. coli* host cells (containing an individual truncate) of the stock culture were grown under the following conditions. Sixteen liters of media (11 liters LB Millers and 5 liters BHI; commercially available) were autoclaved and placed in a 20 liter fermentor (New Brunswick Bioflow IV). Culturing conditions of the fermentor are a constant temperature of 37° C., pH 7.4, agitation 500 rpm and $DO_2$ 100%–25%. The media was inoculated with 500 ml of stock culture and Kanamycin. At an O.D. of 1.0–1.5, 0.25 mM IPTG was added.

After the IPTG was added, the culture was maintained for about 1 hour and the *E. coli* host cells were harvested in CEPA LE continuous flow centrifuge. The dry weight of the pellet was a yield of about 50–75 grams of cells.

The pellet was placed in a container on ice and to prepare the periplasm there was added per gram of cells: 4 ml 20% sucrose/20 mM Tris 8.0; 200 μl EDTA 8.0; and 40 μl lysozyme (10 mg/ml). After such addition the mixture was maintained on ice for about 20 minutes. Then 160 μl of 0.5 M $MgCl_2$ was added to the mixture and the mixture was centrifuged at 12,000 g. The supernatant was brought to 75% $NH_4SO_4$ and then centrifuged for at least 2 hours (preferably overnight). The $NH_4SO_4$ pellet was then centrifuged at 12,000 g for 30 minutes and dialyzed against 20 mM KMES pH 6.1 for T2 and 20 mM Tris pH 8.4 for each of T3–T5.

Each of the T2 and T3–T5 samples was purified by nickel chromatography, followed by anion (T2) and Cation (T3–T5) Exchange chromatography, as required. Ni-NTA Agarose Beads (Qiagen) were added at 1:25 by volume to the dialysate followed by rocking for at least two hours (preferably overnight) in a conical tube. The mixture was then centrifuged at 2000 g with no brake and the supernatant was pulled off. This was repeated with 5×washing with 20 mM Tris pH 8.0. Then one bead volume of 100 mM EDTA in 20 mM Tris pH 8.0 was added and rocked for at least two hours (preferably overnight). The mixture was gently spun by centrifugation and the supernatant containing the one of the FimH truncate T2–T5 was pulled off. If the supernatant contained T2 it was dialyzed into 20 mM KMES pH 6.1, but when the supernatant contained one of the T3–T5 truncates it was dialyzed into 20 mM Tris pH 8.4.

The T2 was purified by anion exchange chromatography of the dialyzate. Samples of the dialyzate were injected onto a Pharmacia Source 15 Q column at a rate of 1.5 milliliters per minute; A: 20 mM Tris pH 8.4 B: 20 mM Tris pH 8.4/1M NaCl. The run gradient of 0–40% over 80 ml, 40–100% over 20 ml was utilized. The truncate was eluted at around 100–200 mM salt.

Further purification was done by a final dialysis into 20 mM Tris pH 8.0. The yield was an average of 3–5 mg/50 liters.

Each of the T3–T5 truncates was purified by anion exchange chromatography of the dialyzate. Samples of the dialyzate were injected onto a Pharmacia Source S 10/10HR column at a rate of 1.5 milliliters per minute; A: 20 mM KMES pH6.1 B: 20 mM KMES 6.1/1M KCL. The run gradients of 0–40% over 80 ml and 40–100% over 20 ml were utilized. The individual truncate being processed was eluted at around 100–200 mM salt. Further purification was done by a final dialysis into 20 mM Tris pH 8.0. The yield was an average of 3–5 mg/50 liters.

The identity of the each of the protein fragments T2–T5 was confirmed by Western Blot for the truncate fragment lengths (after cleavage of the signal sequence) 160, 165, 175 and 186, respectively (data not shown).

EXAMPLE 13

Recombinant Expression and Purification of Full-Length His-tag FimH by Nickel and Anion/Cation Chromatography A polynucleotide encoding FimH as in Example 12, above, (cloned into pMMB91 plasmid as EcoRI/BamHI with IPTG promoter, His-tag and Kanamycin resistance; commercially available plasmid vector, other readily obtainable functionally equivalent vectors may also be used) and a polynucleotide encoding FimC (as in Example 10, above) can be co-inserted into the same E. coli strain described in Example 12, above, essentially as in Examples 10 and 12. The procedures set forth in Example 12 are available to isolate the FimCH complex. FimH is then isolated from the FimCH complex.

EXAMPLE 14

Recombinant Expression and Purification of PapD/ PapG (PapDG) By Galα(1–4)Gal and Anion Exchange Chromatography Polynucleotides encoding PapD/PapG (PapDG) in a plasmid vector (commercially available pMMB91 with a tac pomoter and Kanamycin resistance having the PapD and PapG genes inserted, thus by standard methods; other plasmid vectors are commercially available), were inserted into an E. coli strain C600 under standard calcium chloride conditions to produce strain C600/pJP1. A stock culture of the E. coli strain with its inserts was then obtained for use as a fermentation inoculate.

The E. coli host cells of the stock culture were cultured in 16 liters of media (11 liters LB Millers and 5 liters BHI; commercially available) was previously autoclaved and placed in a 20 liter fermentor (New Brunswick Bioflow IV). Culturing conditions of the fermentor are a constant temperature of 37° C., pH 7.4, agitation 500 rpm and $DO_2$ 90%–25%. The media was inoculated with 500 ml of stock culture to provide a starting optical density (O.D.) of 0.1. At about 2–3 hours and an O.D. of 0.6 was observed. Then at an O.D. of 1.2, 0.25 mM IPTG was added.

After the IPTG was added, the culture was maintained for about 1 hour and the E. coli host cells were harvested in CEPA LE continuous flow centrifuge. The dry weight of the pellet was a yield of about 75–100 grams of cells.

The pellet was placed in a container on ice and to prepare the periplasm there was added per gram of cells: 4 ml 20% sucrose/20 mM Tris 8.0; 200 pl EDTA 8.0; and 40 µpl lysozyme (10 mg/ml). After such addition the mixture was maintained on ice for about 20 minutes. Then 160 µl of 0.5 M $MgCl_2$ was added to the mixture and the mixture was centrifuged at 12,000 g. The supernatant was brought to 75% $NH_4SO_4$ and then centrifuged for at least 2 hours (preferably overnight). The $NH_4SO_4$ pellet was then centrifuged at 12,000 g for 30 minutes and dialyzed against 1×PBS fully.

PapDG was purified by chromatography, affinity chromatography followed by anion exchange chromatography. In particular, Galα(1–4)Gal-sepharose beads were added to the filtered dialysate at 1:25 by volume followed by rocking for at least two hours (preferably overnight) in a 50 ml conical tube. The mixture was then centrifuged at 2000 g with no brake and the supernatant was pulled off. This was repeated with 5×washing with 1×pBS. Then one volume of 5 mg/ml Galα(14)Gal was added and rocked at 4° C. for at least two hours (preferably overnight). The mixture was gently spun by centrifugation and the supernatant containing PapDG was pulled off and dialyzed into 20 mM Tris pH 8.0.

Samples of the dialyzate obtained by the above procedures were injected on Pharmacia XK16/10 15Q Source Column at a rate of 2 ml/min, A: 20 mM Tris pH 8.5 B: 20 mM Tris pH 8.6/0.6 M NaCl. The run gradient was 0–30% over 100 ml, 30–100% over 10 ml. PapDG was eluted at around 100–200 mM NaCl. Further processing of the eluted PapDG was done by dialysis with 20 mM Tris pH 8.0. The yields from such procedure were an average of 2 mg PapDG per 50 liters.

The data from the above examples indicate that the binding of FimH to a receptor that is exposed on the luminal surface of both the human and mouse bladder epithelium is critical for uropathogenic E. coli strains to colonize the bladder and cause cystitis. Further immunization of mice to produce IgG to FimH in a mouse model of UTIs blocks the colonization of type 1 piliated bacteria in vivo. Therefore, such immunization protects mice against a mucosal infection of the bladder and subsequent ascending urinary tract infections.

Prevention of other types of bacteria from binding to mucosal surfaces may also be possible by utilizing the above-described vaccines due to significant cross-reactivity of various bacteria species with regard to adhesin proteins.

Numerous modifications and variations of the present invention are possible in light of the above teachings and, therefore, within the scope of the appended claims, the invention may be practiced otherwise than as particularly described.

What is claimed is:

1. A vaccine comprising a complex selected from the group consisting of FimC-FimH and PapD-PapG, said complex being in a pharmaceutically acceptable carrier and said vaccine eliciting production of an antibody against said complex when administered to a patient in need thereof.

2. The vaccine of claim 1 wherein said FimH arid PapG are selected from the group consisting of recombinant FimH and PapG.

3. The vaccine of claim 1 wherein the complex is FimC-FimH.

4. The vaccine of claim 1 wherein the complex is PapD-PapG.

5. The vaccine of claim 1 further comprising an adjuvant.

6. The vaccine of claim 2 wherein said antibody is specific to the FimH or PapG portion of said complex.

7. The vaccine of claim 1 wherein said antibody interferes with binding to mammalian cells by pilus-beanng bacteria.

8. The vaccine of claim 7 wherein said bacteria are bacteria of the family Enterobacteriaceae.

9. The vaccine of claim 8 wherein said bacteria are *Escherichia coli* bacteria.

10. A process for protecting against a bacterial infection caused by pilus-bearing bacteria in a human being, comprising administering to a human being at risk of such infection a protective amount of the vaccine of claim 1.

11. The process of claim 10 wherein said bacterial infection is caused by bacteria of the family Enterobacteriaceae.

12. The process of claim 11 wherein said bacteria are *Escherichia coli* bacteria.

13. The process of claim 10 wherein said infection is a urinary tract infection.

14. The process of claim 10 wherein said infection is a bladder infection.

15. A process for treating an infection caused by pilus-bearing bacteria in a human being comprising administering to a human being afflicted with said infection a therapeutically effective amount of the vaccine of claim 1.

16. The process of claim 15 wherein said infection is caused by bacteria of the family Enterobacteriaceae.

17. The process of claim 16 wherein said bacteria are *Escherichia coli* bacteria.

18. The process of claim 15 wherein said infection is a urinary tract infection.

19. The process of claim 15 wherein said infection is a bladder infection.

20. A process for eliciting an antibody response in a mammal comprising administering to said mammal the vaccine of claim 2 in an amount sufficient to elicit production in said mammal of an antibody against the FimH or PapG portion of said vaccine.

21. The process of claim 20 wherein said mammal is a mouse.

22. The process of claim 20 wherein said mammal is a human being.

23. A process for protecting against a bacterial infection caused by pilus-bearing bacteria in a human being, comprising administering to a human being at risk of such infection a protective amount of the vaccine of claim 3.

24. The process of claim 23 wherein said bacterial infection is caused by bacteria of the family *Enterobacteriaceae*.

25. The process of claim 24 wherein said bacteria are *Escherichia coli* bacteria.

26. The process of claim 23 wherein said infection is a urinary tract infection.

27. The process of claim 23 wherein said infection is a bladder infection.

28. A process for treating an infection caused by pilus-bearing bacteria in a human being comprising administering to a human being afflicted with said infection a therapeutically effective amount of the vaccine of claim 3.

29. The process of claim 28 wherein said infection is caused by bacteria of the family *Enterobacteriaceae*.

30. The process of claim 29 wherein said bacteria are *Escherichia coli* bacteria.

31. The process of claim 28 wherein said infection is a urinary tract infection.

32. The process of claim 28 wherein said infection is a bladder infection.

33. A process for eliciting an antibody response in a mammal comprising administering to said mammal the vaccine of claim 3 in an amount sufficient to elicit production in said mammal of an antibody against the FimH portion of said vaccine.

34. The process claim 33 wherein said mammal is a mouse.

35. The process of claim 35 wherein said mammal is a human being.

36. The vaccine of claim 3 wherein FimH is recombinant FimH.

37. The vaccine of claim 4 wherein PapG is recombinant PapG.

\* \* \* \* \*

UNITED STATES PATENT AND TRADEMARK OFFICE
CERTIFICATE OF CORRECTION

PATENT NO. : 6,500,434 B1
DATED : December 31, 2002
INVENTOR(S) : Solomon Langermann It is certified that error appears in the above-identified patent and that said Letters Patent is hereby corrected as shown below:

Column 3,
Line 41, delete "of the their" and insert therefor -- of their --

Figure 3B:
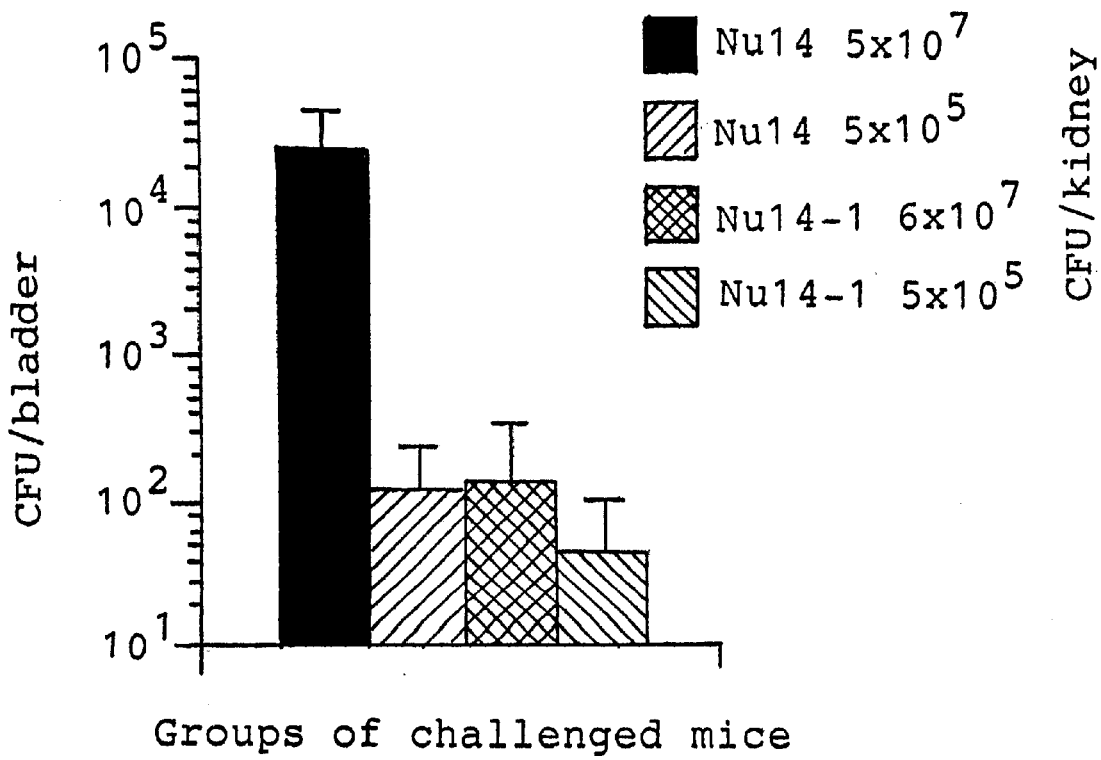

Column 4,
Line 27, delete "FIG. 2" and insert therefor -- Figure 2A --
Line 35, delete "FIGS. 3-3E" and insert therefor -- Figures 3A-3E --
Line 38, delete "FIGS. 3 and 3B" and insert therefor -- Figures 3A and 3B --

Column 6,
Line 18, delete "wetting agent" and insert therefor -- wetting agents --

Column 10,
Line 43, delete "pNH8" and insert therefor -- pNH8A --
Line 43, delete "pNH18, pNH46" and insert therefor -- pNH18A, pNH46A --

Column 14,
Line 59, delete "(FIG. 1)" and insert therefor -- (Figure 1A) --
Line 63, delete "FIGS. 1 and 1B" and insert therefor -- Figures 1A and 1B --

Column 16,
Line 23, delete "FIG. 2" and insert therefor -- Figure 2A --

Column 18,
Line 6, delete "C3 H" and insert therefor -- C3H --

Column 20,
Line 59, delete "pH7.0/0.6 M" and insert therefor -- pH7.0/0.6M --

Column 21,
Line 17, delete "2000 g" and insert therefor -- 2000g --

Column 23,
Line 42, delete "200 pl EDTA" and insert therefor -- 200 $\mu$l EDTA --
Line 42, delete "40 $\mu$pl" and insert therefor -- 40 $\mu$l --

UNITED STATES PATENT AND TRADEMARK OFFICE
CERTIFICATE OF CORRECTION

PATENT NO. : 6,500,434 B1
DATED : December 31, 2002
INVENTOR(S) : Solomon Langermann It is certified that error appears in the above-identified patent and that said Letters Patent is hereby corrected as shown below:

Column 27,
Line 30, delete "pilus-beanng" and insert therefor -- pilus-bearing --

Signed and Sealed this

Twentieth Day of May, 2003

JAMES E. ROGAN
*Director of the United States Patent and Trademark Office*